US00PP31432P2

(12) United States Plant Patent
van der Meer

(10) Patent No.: US PP31,432 P2
(45) Date of Patent: Feb. 4, 2020

(54) ***ASTILBE* PLANT NAMED 'MOJITO'**

(50) Latin Name: *Astilbe japonica*
Varietal Denomination: Mojito

(71) Applicant: Hans van der Meer, Nieuwe Wetering (NL)

(72) Inventor: Hans van der Meer, Nieuwe Wetering (NL)

(73) Assignee: COMPASS PLANTS B.V., Hillegom (NL)

( * ) Notice: Subject to any disclaimer, the term of this patent is extended or adjusted under 35 U.S.C. 154(b) by 0 days.

(21) Appl. No.: 16/350,789

(22) Filed: Jan. 12, 2019

(51) Int. Cl.
*A01H 5/02* (2018.01)
*A01H 6/80* (2018.01)

(52) U.S. Cl.
USPC ..... Plt./407

(58) Field of Classification Search
USPC ..... Plt./407
See application file for complete search history.

*Primary Examiner* — Susan McCormick Ewoldt
(74) *Attorney, Agent, or Firm* — C. A. Whealy

(57) ABSTRACT

A new and distinct cultivar of *Astilbe* plant named 'Mojito', characterized by its relatively compact, broadly upright and mounding plant habit; moderately vigorous growth habit; dark green-colored leaves; freely and uniformly flowering habit; white-colored flowers on upright and strong peduncles; and good container and garden performance.

2 Drawing Sheets

Botanical designation: *Astilbe japonica.*
Cultivar denomination: 'MOJITO'.

BACKGROUND OF THE INVENTION

The present invention relates to a new and distinct cultivar of *Astilbe*, botanically known as *Astilbe japonica* and hereinafter referred to by the name 'Mojito'.

The new *Astilbe* plant is a product of a planned breeding program conducted by the Inventor in Nieuwe Wetering, The Netherlands. The objective of the breeding program was to create new uniform and freely flowering *Astilbe* plants with attractive leaf and flower coloration.

The new *Astilbe* plant originated from an open-pollination in 2010 in Nieuwe Wetering, The Netherlands, of *Astilbe japonica* 'Ellie', not patented, as the female, or seed, parent with an unknown *Astilbe japonica* seedling selection as the male, or pollen, parent. The new *Astilbe* plant was discovered and selected by the Inventor as a single flowering plant from within the progeny of the stated open-pollination in a controlled greenhouse environment in Nieuwe Wetering, The Netherlands during the summer of 2012.

Asexual reproduction of the new *Astilbe* plant by vegetative divisions in a controlled nursery environment in Nieuwe Wetering, The Netherlands since December, 2012, has shown that the unique features of this new *Astilbe* plant are stable and reproduced true to type in successive generations.

SUMMARY OF THE INVENTION

Plants of the new *Astilbe* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'Mojito'.

These characteristics in combination distinguish 'Mojito' as a new and distinct *Astilbe* plant:

1. Relatively compact, broadly upright and mounding plant habit.
2. Moderately vigorous growth habit.
3. Dark green-colored leaves.
4. Freely and uniformly flowering habit.
5. White-colored flowers on upright and strong peduncles.
6. Good container and garden performance.

Plants of the new *Astilbe* differ primarily from plants of the female parent, 'Ellie', in the following characteristics:

1. Plants of the new *Astilbe* are more compact than plants of 'Ellie'.
2. Leaves of plants of the new *Astilbe* are smaller than leaves of plants of 'Ellie'.
3. Plants of the new *Astilbe* flower more uniformly than plants of 'Ellie'.
4. Peduncles of plants of the new *Astilbe* are lighter green in color than peduncles of plants of 'Ellie'.

Plants of the new *Astilbe* can be compared to plants of *Astilbe japonica* 'Vision in White', disclosed in U.S. Plant Pat. No. 18,965. In side-by-side comparisons, plants of the new *Astilbe* and 'Vision in White' differ in the following characteristics:

1. Plants of the new *Astilbe* are more compact than plants of 'Vision in White'.
2. Plants of the new *Astilbe* are more freely and more uniformly flowering than plants of 'Vision in White'.
3. Inflorescences of plants of the new *Astilbe* are larger than inflorescences of plants of 'Vision in White'.

BRIEF DESCRIPTION OF THE PHOTOGRAPHS

The accompanying colored photographs illustrate the overall appearance of the new *Astilbe* plant showing the colors as true as it is reasonably possible to obtain in colored reproductions of this type. Colors in the photographs may differ slightly from the color values cited in the detailed botanical description which accurately describe the colors of the new *Astilbe* plant.

The photograph on the first sheet is a side perspective view of a typical flowering plant of 'Mojito' grown in a container.

The photograph on the second sheet is a close-up view of typical inflorescences of 'Mojito'.

DETAILED BOTANICAL DESCRIPTION

The aforementioned photographs and following observations, measurements and values describe plants grown during the spring and early summer in 15-cm containers in an outdoor nursery in Nieuwe Wetering, The Netherlands and under cultural practices typical of commercial *Astilbe* production. During the production of the plants, day temperatures ranged from 25° C. to 30° C. and night temperatures ranged from 15° C. to 20° C. Plants were one year old when the photographs and description were taken. In the following description, color references are made to The Royal Horticultural Society Colour Chart, 2015 Edition, except where general terms of ordinary dictionary significance are used.

Botanical classification: *Astilbe japonica* 'Mojito'.

Parentage:

- *Female, or seed, parent.*—*Astilbe japonica* 'Ellie', not patented.
- *Male, or pollen, parent.*—Unknown *Astilbe japonica* seedling selection, not patented.

Propagation:

- *Type.*—By vegetative divisions.
- *Time to initiate roots.*—About three weeks at temperatures about 20° C.
- *Root description.*—Thick, fleshy; typically brown in color, actual color of the roots is dependent on substrate composition, water quality, fertilizer type and formulation.
- *Rooting habit.*—Freely branching; dense.

Plant description:

- *Plant form and growth habit.*—Herbaceous perennial; relatively compact, broadly upright and mounding plant form with inflorescences held above the foliar plane; flowering stems and leaves basal; freely flowering with numerous basal branches developing per plant, dense and bushy; moderately vigorous growth habit; and freely and uniformly flowering habit.
- *Growth rate.*—Moderately rapid; from divisions, about six months are required to produce fully-grown flowering plants in containers.
- *Plant height* (*soil level to top of foliar plane*).—About 43.5 cm.
- *Plant height* (*soil level to top of inflorescences*).—About 64 cm.
- *Plant width* (*spread*).—About 65.6 cm.
- *Stem description.*—Length: About 30.3 cm. Diameter: About 3 mm. Internode length: About 13.5 cm. Strength: Strong. Aspect: Erect to about 10° from vertical. Texture and luster: Sparsely pubescent; glossy. Color, developing: Close to 146A to 146B. Color, developed: Close to 146C; towards the base, close to 146A to 146B.

Leaf description:

- *Arrangement.*—Alternate; biternately compound; about 47 leaflets per leaf.
- *Leaf length* (*excluding petiole*).—About 25.1 cm.
- *Leaf width.*—About 25.8 cm.
- *Terminal leaflet length.*—About 7.5 cm.
- *Terminal leaflet width.*—About 3.7 cm.
- *Lateral leaflet length.*—About 6.2 cm.
- *Lateral leaflet width.*—About 2.4 cm.
- *Leaflet shape.*—Obovate to elliptic.
- *Leaflet apex.*—Apiculate.
- *Leaflet base.*—Attenuate to rounded.
- *Leaflet margin.*—Biserrate.
- *Leaflet texture and luster, upper and lower surfaces.*—Moderately pubescent; slightly rugose; slightly glossy.
- *Leaflet venation pattern.*—Pinnate.
- *Leaflet color.*—Developing leaflets, upper surface: Close to between 137B and 143A. Developing leaflets, lower surface: Close to 138A to 138B. Fully expanded leaflets, upper surface: Darker than between NN137A and 147A; venation, close to 146C. Fully expanded leaflets, lower surface: Close to 147A to 147B; venation, close to 146D.
- *Leaf petiole length.*—About 30.9 cm.
- *Leaf petiole diameter.*—About 2.25 cm.
- *Leaf and leaflet petiole strength.*—Strong.
- *Leaf and leaflet petiole texture and luster, upper and lower surfaces.*—Sparsely pubescent; glossy.
- *Leaf and leaflet petiole color, upper surface.*—Close to between N199B and N199C; at the nodes, close to 178A to 178B.
- *Leaf and leaflet petiole color, lower surface.*—Close to 199A to 199B and N199B.

Flower description:

- *Flower type and flowering habit.*—Single rotate flowers arranged on terminal compound panicles; flowers face upright, outward or downward depending on position on the inflorescence; panicles broadly conical in shape; freely and uniformly flowering habit with about 1,500 flowers developing per inflorescence.
- *Fragrance.*—Moderate; sweet and pleasant.
- *Natural flowering season.*—Plants begin flowering about 13 weeks after planting; continuously flowering from late spring until late summer in The Netherlands.
- *Postproduction longevity.*—Flowers last about ten days on the plant; flowers not persistent.
- *Flower buds.*—Height: About 2 mm. Diameter: About 1.5 mm. Shape: Broadly elliptic. Texture and luster: Smooth, glabrous; matte. Color: Close to 145A to 145C.
- *Inflorescence height.*—About 23.6 cm.
- *Inflorescence diameter.*—About 14.2 cm.
- *Flower diameter.*—About 1.1 cm.
- *Flower depth.*—About 4 mm.
- *Petals.*—Quantity per flower: Typically five in a single whorl. Length: About 4 mm. Lobe width: About 1 mm. Shape: Oblanceolate; slightly recurved. Apex: Acute. Base: Narrowly cuneate. Margin: Entire. Texture and luster, upper and lower surfaces: Smooth, glabrous; matte. Color: Developing petals, upper and lower surfaces: Close to NN155D. Fully expanded petals, upper and lower surfaces: Close to NN155D; color does not change with development.
- *Sepals.*—Quantity per flower: Typically five in a single whorl, fused towards the base forming a campanulate-shaped calyx. Length: About 2 mm. Width:

About 1 mm. Shape: Broadly ovate. Apex: Acute. Base: Cuneate, fused. Margin: Entire. Texture and luster, upper and lower surfaces: Smooth, glabrous; matte. Color: Developing sepals, upper and lower surfaces: Close to NN155A. Fully expanded sepals, upper and lower surfaces: Close to NN155B.

*Peduncles*.—Length: About 23.4 cm. Diameter: About 1.75 mm. Angle: Mostly erect. Strength: Strong. Texture and luster: Moderately pubescent; slightly glossy. Color: Close to 145A.

*Pedicels*.—Length: About 1 mm. Diameter: About 0.5 mm. Angle: About 40° from peduncle axis. Strength: Moderately strong. Texture and luster: Moderately to densely pubescent; matte. Color: Close to NN155C.

*Reproductive organs*.—Stamens: Quantity per flower: Typically ten; anthers basifixed. Filament length: About 3.5 mm. Filament color: Close to NN155D. Anther shape: Broadly ovate. Anther length: About 0.5 mm. Anther diameter: About 0.2 mm. Anther color: Close to 155C. Pollen amount: Moderate. Pollen color: Close to 155A. Pistils: Quantity per flower: Two. Pistil length: About 1 mm. Stigma diameter: About 0.1 mm. Stigma shape: Club-shaped. Stigma color: Close to NN155C. Style length: About 1 mm. Style color: Close to NN155C. Ovary color: Close to NN155C.

*Seeds and fruits*.—To date, seed and fruit development have not been observed on plants of the new *Astilbe*.

Pathogen & pest resistance: To date, plants of the new *Astilbe* have not been noted to be resistant to pathogens and pests common to *Astilbe* plants.

Garden performance: Plants of the new *Astilbe* have been observed to have good garden performance and tolerate rain, wind and high temperatures of about 35° C. Additionally, plants of the new *Astilbe* have been observed to be suitable for USDA Hardiness Zones 5 through 10.

It is claimed:

1. A new and distinct *Astilbe* plant named 'Mojito' as illustrated and described.

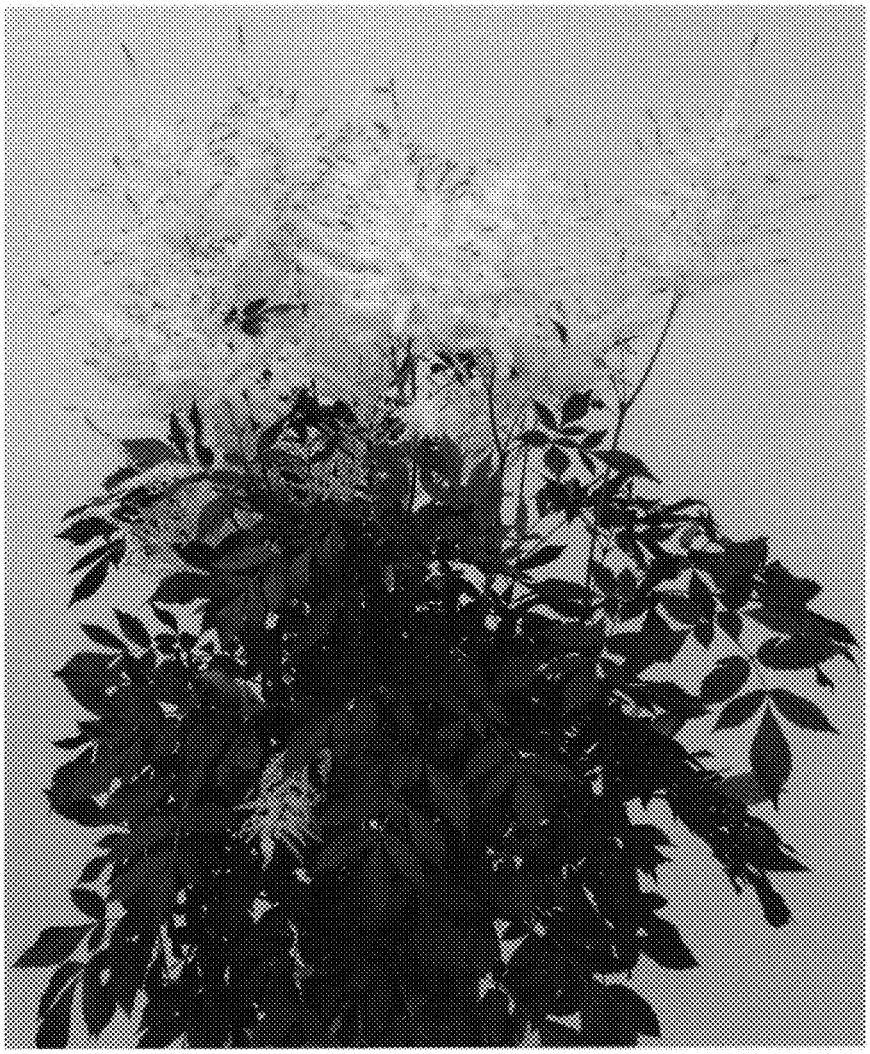

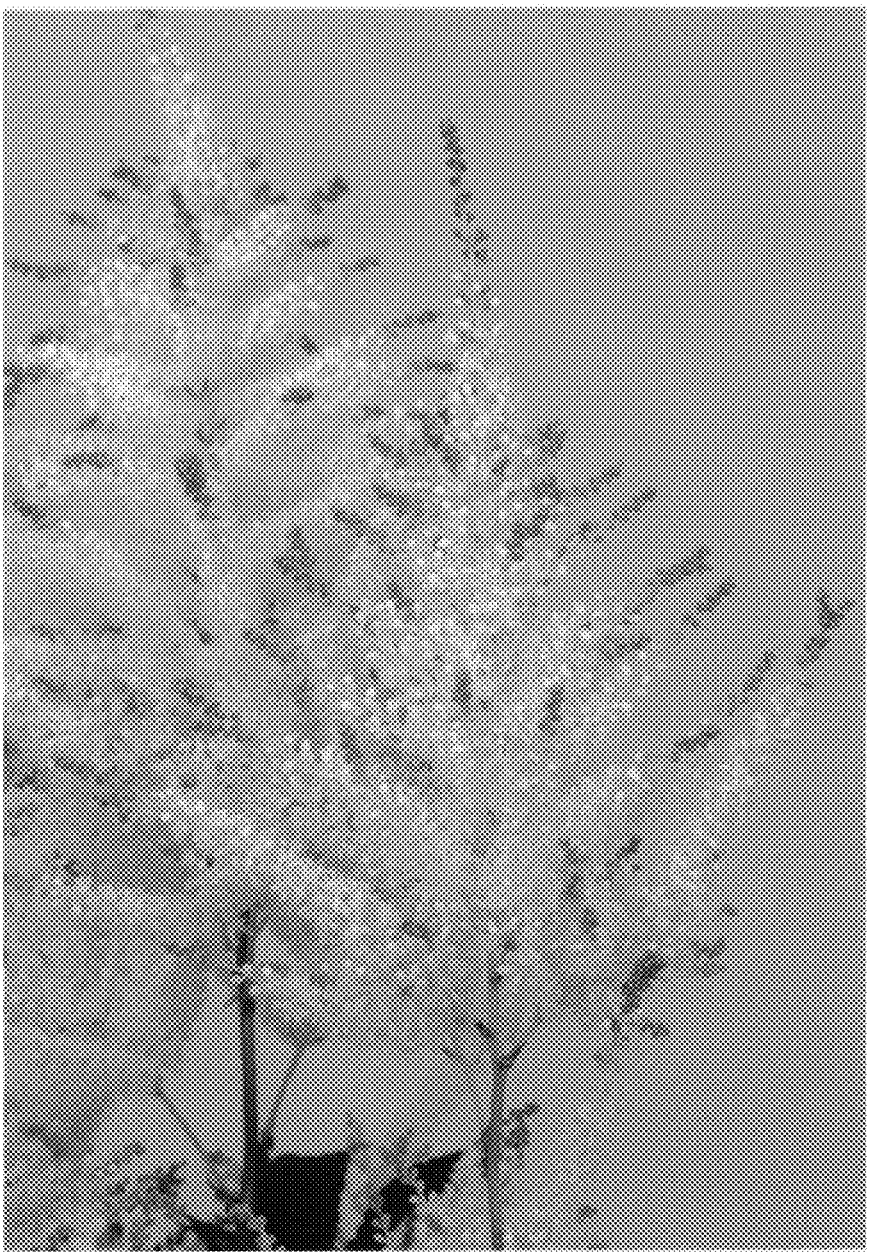

* * * * *